United States Patent [19]

Urbanec et al.

[11] Patent Number: 5,076,283
[45] Date of Patent: Dec. 31, 1991

[54] METHOD AND APPARATUS FOR MIXING OF FLUIDS

[76] Inventors: Kenneth A. Urbanec, 3813 Dickey Rd., Gibsonia, Pa. 15044; Tin-Kan Hung, 3918 Hickory Hill Rd., Murrysville, Pa. 15668

[21] Appl. No.: 506,173
[22] Filed: Apr. 9, 1990
[51] Int. Cl.$^5$ ............................................. A61B 5/00
[52] U.S. Cl. ................................................. 128/763
[58] Field of Search ............... 128/760, 763, 771, 770; 604/416, 260, 266, 269

[56] References Cited

U.S. PATENT DOCUMENTS

| | | | |
|---|---|---|---|
| 3,942,514 | 3/1976 | Ogle | 128/764 |
| 4,384,581 | 5/1983 | Conway . | |
| 4,469,482 | 9/1984 | Lissenburg et al. . | |
| 4,687,000 | 8/1987 | Eisenhardt et al. | 128/760 |
| 4,713,060 | 12/1987 | Riuli . | |

Primary Examiner—Max Hindenburg
Attorney, Agent, or Firm—Clifford A. Poff

[57] ABSTRACT

An assembly for maintaining a fluid sample in a homogeneous state. The assembly includes a mechanical mixer comprised of an annular ring positioned within a collection chamber of the assembly. The annular ring is comprised of a material compatible to the fluid and having a density less than that of the fluid to be collected in the collection chamber. By inverting the assembly once the fluid sample has been collected within the collection chamber, the annular ring forming the mechanical mixer is caused to be translated through the fluid to float on a top surface of the fluid. Translation of the annular ring through the fluid causes mixing of the fluid to thereby maintain the fluid in a homogeneous state.

3 Claims, 2 Drawing Sheets

METHOD AND APPARATUS FOR MIXING OF FLUIDS

BACKGROUND OF THE INVENTION

1. Field of the Invention

The present invention relates generally to method and apparatus for the mechanical mixing of fluid samples, and, more particularly, to an assembly having a mechanical mixer positioned within an internal collection chamber of the assembly for maintaining the fluid sample in a homogenous state.

2. Description or the Prior Art

The maintenance of a mixture of solid particles and fluid in a homogeneous state is required for a wide assortment of medical and industrial applications. For example, the need to extract body fluids from an individual for medical testing purposes is well known and widespread. Many apparatus are known in the art for aspirating or otherwise extracting bodily fluids from the subject. Various types of syringe assemblies are disclosed in, for example, U.S. Pat. Nos. 4,384,581; 4,469,482; and 4,713,060. The syringe disclosed in each of the aforementioned patents, as well as many other conventional prior art syringe assemblies include a hypodermic needle of suitable sharpness for puncturing the dermis layer of the subject, and for aspirating a desired bodily fluid from the subject. An end portion of the hypodermic needle is coupled to a collection chamber formed by a barrel portion of the syringe assembly whereat the fluid aspirated by the hypodermic needle is collected. Many syringe assemblies further include a plunger assembly for creating a vacuum to aid in the aspiration of the fluid from the subject.

One such fluid frequently aspirated from a subject for purposes of medical testing is blood. Blood samples of a subject are collected for such purposes as drug and alcohol testing, testing for disease, and detecting the levels of certain blood components. A blood sample from a subject is oftentimes collected for purposes of arterial blood gas analysis for the purpose of testing for cardiac sufficiency. A primary test for cardiac disfunction requires the collection of a blood sample from a subject for purposes of measuring oxygen content of the blood. Cardiac disfunction oftentimes results in the failure of oxygen supply, through blood, to body tissue. In order to insure that a specimen taken from a blood sample is a representative specimen of the blood taken from the subject, the blood sample must be collected under anaerobic conditions, and the blood must be maintained in a homogenous state. Blood is actually comprised of a liquid, plasma portion, and a solid portion consisting of blood cells and platelets. Because the specific gravity of the blood cells and platelets is greater than that of the liquid plasma, the solid portions of the blood mixture tends to settle out of the mixture. When taking specimens of the blood sample, once collected, is in imperative that the blood sample be homogenous in order to insure that a representative specimen is taken from the sample to thereby allow accurate analysis to be performed.

One quick prior art method for maintaining the blood sample in a state of homogeneity is to merely shake the syringe assembly, once the sample has been collected, and the syringe assembly has been removed from the subject. Other prior art apparatus for maintaining the blood sample in homogeneity includes machinery similar to "test-tube shakers" for shaking the blood sample to maintain the solid portions of the blood in solution with the liquid portions thereof.

Although accurate, the mechanical shaking machinery requires an additional step, and, hence, additional time to insure that the blood sample is maintained in a state of homogeneity. And such machinery quite commonly causes trauma and other damage to the blood samples.

Similar devices are used in industry for the research, development and testing of consumer products such as cosmetics, paints, medicines, and the like. Accordingly, such agitator devices suffer from the same shortcomings as their counterparts used in medical laboratories.

It is, accordingly, an object of the present invention to provide a method and apparatus for maintaining a suspension or multilayered fluids to a state of homogeneity to allow accurate testing of representative portions thereof.

It is a further object of the present invention to provide a syringe assembly for the aspiration and collection of a fluid sample, and for mixing the fluid sample, once sedimentation or stratification has developed, to a homogenous state.

It is a yet further object of the present invention to provide apparatus for a syringe assembly for mixing a fluid sample collected in a collection chamber of a syringe assembly to thereby maintain a fluid sample in a homogenous state.

Still other objects and advantages will become apparent in light of the attached drawings and written description of the invention presented herebelow.

SUMMARY OF THE INVENTION

In accordance with the present invention, an assembly for mixing a suspension fluid sample or multilayered fluid to homogeneity in a container for allowing a homogenous specimen to be taken therefrom is disclosed. In a preferred embodiment, the assembly comprises a syringe assembly for collecting body fluids from a subject. The syringe assembly includes a means forming a barrel having an internal collection chamber for the collection of fluid samples therein, means for aspirating the fluid sample into the internal collection chamber, and means positioned within the internal chamber for maintaining the fluid sample, once collected in the internal chamber, in homogeneity, such that any portion of the fluid sample may be utilized as the homogenous specimen.

In the preferred embodiment, the means positioned within the internal chamber includes a means forming a mechanical mixer for mechanically mixing the fluid sample. The means forming the mechanical mixer may be comprised of a disk member having diametrical dimensions suitable for allowing placement thereof within the internal chamber. The disk member is preferably formed of an annular disk having a means forming a center aperture for providing fluid flow of the fluid sample into the internal chamber. Preferably, the disk member is comprised of material having a density less than the density of the fluid sample such that inversion of the means forming the barrel, once the fluid sample is collected in the internal collection chamber, causes the disk member to rise thorough the fluid sample to thereby mix the fluid sample and maintain the fluid sample in homogeneity.

In another embodiment, the present invention discloses apparatus positioned within a collection chamber of a hypodermic needle and syringe assembly for maintaining a fluid sample collected in the collection chamber in a homogenous state, wherein the apparatus forms a disk member having diametrical dimensions allowing placement thereof within the collection chamber, and being comprised of a material having a density less than the density of the fluid sample such that inversion of the collection chamber causes the disk member to rise through the fluid sample to thereby mix the fluid sample and maintain the fluid sample in the homogenous state. The apparatus preferably includes an annular disk having a means forming a center aperture providing fluid flow of the fluid sample during collection of the fluid sample in the collection chamber.

In a specific embodiment of the present invention, a syringe assembly is disclosed for collecting a blood sample from a subject comprised of plasma and blood cells, and for maintaining the blood sample in a state of homogeneity for allowing a homogeneous specimen to be taken therefrom. In this specific embodiment, the syringe assembly includes means forming a barrel and having an internal collection chamber for collection of the blood sample therein, a hypodermic needle for aspirating blood from the subject, wherein the hypodermic needle includes an end portion connected to the internal collection chamber for permitting collection of the blood aspirated by the hypodermic needle to be collected in the internal collection chamber, and a means forming a mechanical mixer positioned within the internal collection chamber for maintaining the plasma and blood cells comprising the blood sample in the state of homogeneity such that any portion of the blood sample may be utilized as the homogeneous specimen. Preferably, the means forming the mechanical mixer is comprised of a disk member having diametrical dimensions suitable for allowing placement thereof within the internal chamber. The disk member may preferably be further formed of an annular disk having a means forming a center aperture for providing fluid flow of the fluid sample into the internal chamber. The disk member is preferably comprised of a material compatible to the fluid sample and having a density less than the density of the fluid sample such that inversion of the means forming the barrel, once the fluid sample is collected in the internal collection chamber causes the disk member to rise by buoyant force through the fluid sample to thereby mix the fluid sample and maintain the fluid sample in homogeneity.

The present invention further discloses a method for maintaining a solid-containing fluid sample or multilayered fluid in a homogeneous state within a chamber through the use of an annular disk-like agitator member of less density than the fluid. Inversion of the chamber once the fluid is contained therein causes the agitator to rise in the chamber and through the fluid to maintain the fluid in a state of homogeneity.

The present invention further discloses a method for collecting a fluid sample from a fluid source, and for maintaining the fluid sample, once collected, in homogeneity. The method includes the steps of inserting an end portion of a hypodermic needle into a subject to position the end portion proximate to the fluid source from which the fluid sample is to be collected, aspirating a desired amount of fluid from the fluid source through the hypodermic needle, collecting the fluid aspirated through the hypodermic needle in a collection chamber, wherein the collection chamber contains a means for mixing the fluid sample collected in the collection chamber, and mixing the fluid sample, once collected in the collection chamber, in order to maintain the fluid sample in a homogeneous state. The means for mixing positioned within the collection chamber utilized in the step of collecting includes a means forming a mechanical mixer for mechanically mixing the fluid sample. The means forming the mechanical mixer is preferably comprised of a disk member having diametrical dimensions suitable for allowing placement thereof within the internal chamber, and the disk member preferably is further formed as an annular disk having a means forming a center aperture for providing fluid flow of the fluid sample into the internal chamber. Preferably, the disk member is comprised of a material having a density less than the density of the fluid sample, such that inversion of the means forming the barrel, once the fluid sample is collected in the internal collection chamber, causes the disk member to rise through the fluid sample to thereby mix the fluid sample and maintain the fluid sample in homogeneity.

The method of the present invention preferably includes the further step of removing the end portion of the hypodermic needle from the position proximate to the fluid source after collection of the fluid sample in the collection chamber. In the preferred embodiment of the present invention, the step of mixing the fluid sample includes inverting the collection chamber to thereby cause the disk member to rise by buoyant force through the fluid chamber and to thereby maintain the fluid sample in the homogeneous state.

DESCRIPTION OF THE PREFERRED EMBODIMENTS

Figure 1:
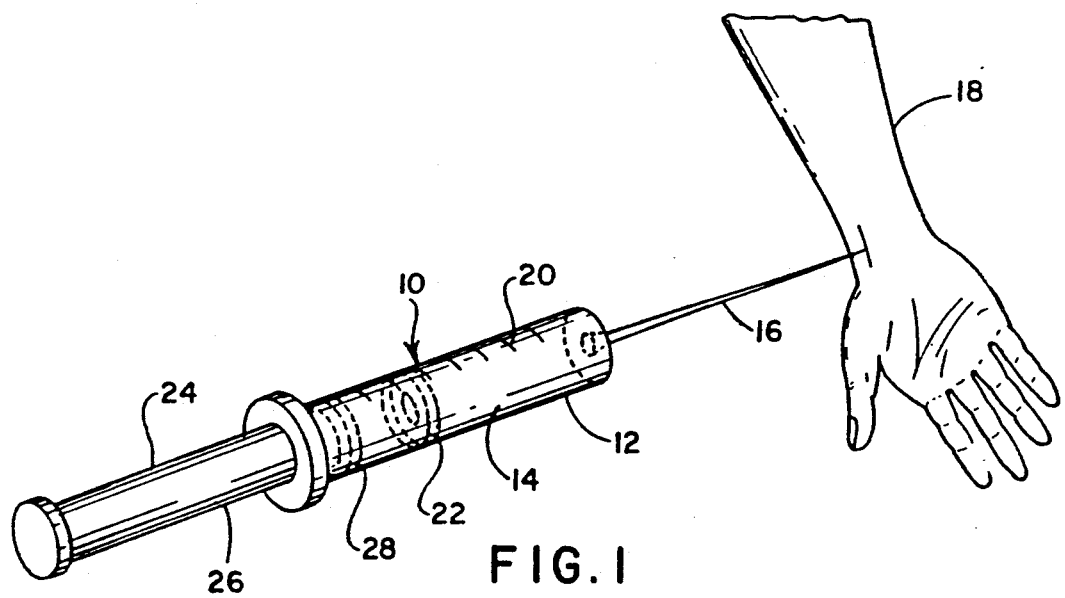
FIG. 1 is a perspective illustration of a first embodiment of a syringe assembly constructed in accordance with the present invention.

Turning first to the perspective illustration of FIG. 1, there is shown a syringe assembly, referred to generally by reference numeral 10, of a first embodiment of the present invention. Syringe assembly 10 is comprised of a central barrel portion 12 defining an internal collection chamber 14. Barrel 12 is enclosed at opposite ends thereof such that collection chamber 14 forms an enclosed area suitable for the collection of a fluid material therein. A first end portion of hypodermic needle 16 is attached to an end portion of barrel 12, and a second end portion of needle 16 is of suitable sharpness to allow puncturing of the dermal layer of a subject from whom a fluid sample is to be collected. For purposes of illustration, the sharp end portion of hypodermic needle 16 in FIG. 1 is illustrated proximate to the radial artery of the arm 18 of a test subject, a site whereat arterial blood gas specimens are most frequently obtained. It is to be noted, of course, that hypodermic needle 16, or a similar device, may be utilized to collect a fluid sample from any desired body location of the test subject.

As illustrated in FIG. 1, barrel portion 12 of syringe assembly 10 is of a generally tubular construction and may include volumetric measurement demarcations 20 along the length thereof to allow measurement of the volume of fluid collected in the collection chamber 14 defined by the dimensions of the barrel 12. Positioned within the interior portion of internal collection chamber 14 is mechanical mixer 22. As will be described more fully hereinbelow, mixer 22 functions to maintain a fluid sample collected in collection chamber 14 in a homogeneous state. Mixer 22 is preferably formed in the shape of an annular ring having diametrical dimensions substantially corresponding to the inner diameter of central barrel 12. The cross-sectional shape of the mixer ring 22 may assume any suitable configuration such as circular, elliptical, oval square, triangular, rectangular, and the like. An elliptical configurations used for illustration (FIGS. 5-8) is most preferred. Mechanical mixer 22 may be suitably formed of, but not limited to, the following materials: polypropylene, neoprene, polyethylene, polyurethane and polyvinyl chloride. Further illustrated in the perspective illustration of syringe assembly 10 of FIG. 1 is plunger 24. Plunger 24 is comprised of shaft portion 26 and piston end portion 28 and functions to create a reduced pressure area within collection chamber 14 to aid in the aspiration of fluid thorough hypodermic needle 16 to allow collection of the fluid in the internal collection chamber 14.

Figure 2:
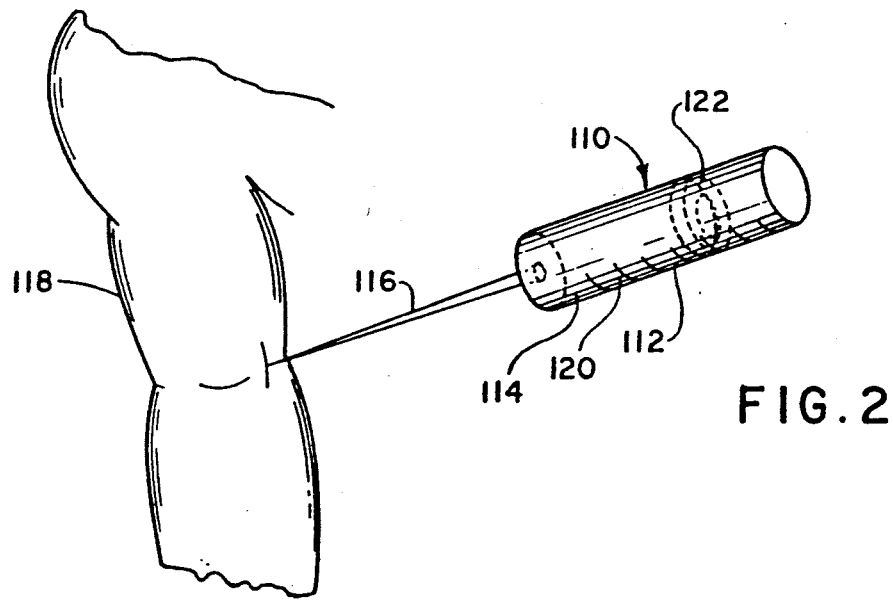
FIG. 2 is a perspective illustration, similar to that of FIG. 1, but illustrating a second embodiment of a syringe assembly according to the present invention.

Turning now to the perspective illustration of FIG. 2, there is shown a second embodiment of a syringe assembly, herein referred to generally by reference numeral 110, constructed according to the teachings of the present invention. Syringe assembly 110 is identical in most respects to syringe assembly 10 FIG. 1, and includes central barrel portion 112 forming an internal collection chamber 114 therewithin. Hypodermic needle 116 possesses a first end portion connected to an interior portion of chamber 114, and a second end portion of suitable sharpness to pierce the dermal layer of a test subject. In this instance, hypodermic needle 116 is shown positioned for penetration of the brachial artery (another common location for obtaining arterial blood gas specimens) in an arm 118 of the test subject. Volumetric measurement demarcations 120 may be formed along the length of the barrel 112 to provide an indication of the volumetric amounts of fluid collected within internal collection chamber 114. Positioned within internal collection chamber 114 is mechanical mixer 122 which, similar to mechanical mixer 22 of FIG. 1, is preferably formed in the shape of an annular ring, and is of diametrical dimension substantially corresponding to the internal diameter of central barrel 112. Syringe assembly 110 of FIG. 2 differs from assembly 10 of FIG. 1 only that plunger 24 is not utilized in order to create a lowered pressure in order to facilitate the aspiration of fluid through the hypodermic needle and into the collection chamber.

Figure 3:
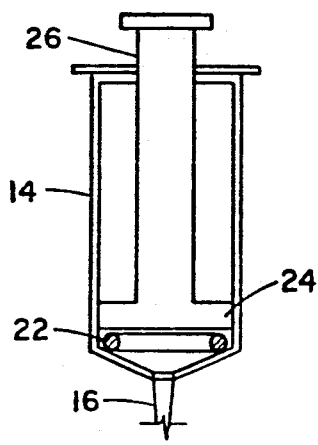
FIG. 3 is a partial sectional view of a portion of the syringe assembly of FIGS. 1 or 2 constructed according to the teachings of the present invention and illustrating a first position of the mechanical mixer contained herein.

Turning now to the cut-away, sectional view of FIG. 3, there is shown a portion of syringe assembly 10. It is to be noted that operation of syringe assembly 110 is identical but for the operation of plunger 24.

As noted hereinabove, when a fluid sample is collected from an human or animal subject, or other fluid supply, a homogeneous mixture is required in order to insure that any portion of the fluid sample collected is representative of the entire sample, thereby providing a representative specimen for testing and other analysis purposes. FIG. 3 illustrates the position of mechanical mixer 22 within collection chamber 14 of syringe assembly 10 prior to aspiration of fluid from a subject through hypodermic needle 16 and into collection chamber 14. As illustrated in FIG. 3, mixer 22 is positioned at a lower portion of collection chamber 14 as gravitational forces causes mechanical mixer 22 to rest against the lowest portion of collection chamber 14.

Figure 4:
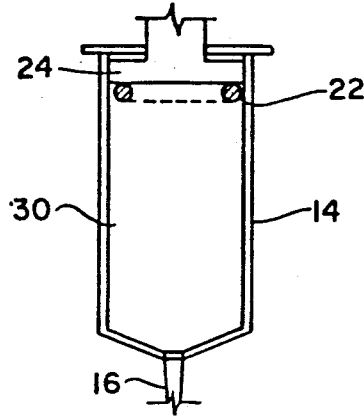
FIG. 4 is a partial sectional view, similar to the view of FIG. 3, illustrating a second position of the mechanical mixer contained within the syringe assembly of the present invention.

Upon puncturing the dermal layer of skin of the subject by hypodermic needle 16, and by retracting plunger 24 through the collection chamber 14, the reduced pressure caused thereby causes the aspiration of fluid into collection chamber 14. Turning to the cut-away, section view of FIG. 4, the fluid aspirated from the subject, and collected in collection chamber 14 is referred to by reference numeral 30.

Figure 4A:
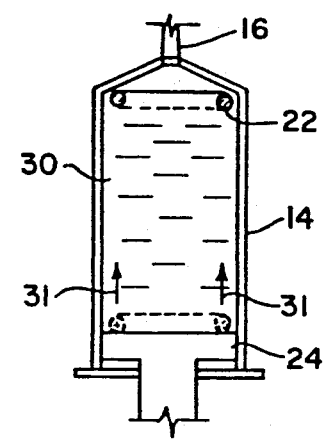
FIG. 4A is an inverted view of the syringe assembly of FIGS. 3 and 4 illustrating the translation of the mechanical mixer during inversion of the syringe assembly.

Mixer 22 is comprised of a material having a density less than that of the fluid 30 collected in collection chamber 14, and is thus caused, as shown by the inverted position of syringe assembly 10 depicted in FIG. 4A, to rise in the direction of arrows 31 through the collection chamber 14 to float on the surface of the fluid material 30. Because mixer 22 is caused to be translated along the length of collection chamber 14 so as to always rest upon the top surface of the fluid 30 collected therewithin, mixing of the fluid material 30 is caused by the agitation and circulation of the fluid due to the rising of mixer 22 and the passage of fluid through a central aperture 32 of the mixer during such translation. The fluid material 30 is thereby effectively maintained in a homogeneous state by simple inversion of the barrel 12. Moreover, occasional reinversion of the barrel 12 will serve to maintain the fluid material in the homogeneous state for an indefinite period of time.

Figure 5:
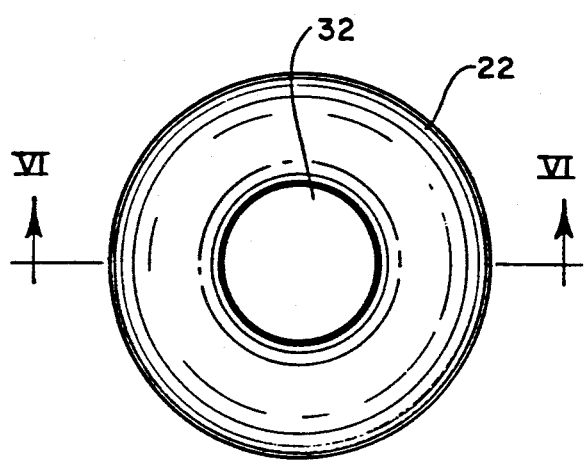
FIG. 5 is a plan view of a preferred embodiment of the mechanical mixer forming a portion of the fluid mixing assembly of the present invention.
Figure 6:
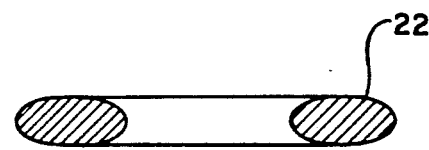
FIG. 6 is a sectional view of the mechanical mixer of FIG. 5 taken along lines VI—VI thereof.

Turning now to the plan view of FIG. 5, there is illustrated in more detail the mechanical mixer 22 which forms a portion of the fluid mixing assembly of the present invention. Again, it is to be noted that mechanical mixer 22 is identical in all respects to mechanical mixer 122 of FIG. 2. As illustrated, mixer 22 is preferably formed in the shape of an annular ring having a center aperture 32. As noted previously, the diametrical dimensions of mixer 22 are selected to correspond with the internal diameter of the barrel 12 forming collection chamber 14. Mixer 22 is preferably formed in the shape of an annular ring having an aperture 32 to aid in the flow of fluid 30 as the fluid is collected in the internal collection chamber 14 during aspiration of fluid from the subject. FIG. 6 is a cross-sectional view taken along lines VI—VI of FIG. 5 and illustrates an embodiment in which mechanical mixer 22 is comprised of a solid-core. As noted hereinabove, mixer 22 is comprised of a material having a specific gravity (i.e., density) less than that of the fluid material 30 to be collected in collection chamber 14.

Figure 7:
FIG. 7 is a sectional, similar to that of FIG. 6, of an alternative embodiment of the mechanical mixer forming a portion of the fluid mixing assembly constructed according to the teachings of the present invention.

FIG. 7 illustrates a cross-sectional view of a mechanical mixer, here referred to as reference numeral 22A. Mechanical mixer 22A is identical in all respects to mechanical mixer 22 except that it has a hollow core. Mechanical mixer 22A of FIG. 7 is advantageous in that the hollow core of the mixer 22A allows an increase in buoyant force or a higher-density material to be selected to form the mixer 22A. Operation of mixer 22A to maintain the fluid material 30 forming the fluid sample in a homogenous state is identical to operation of mechanical mixer 22. Syringe assemblies 10 and 110 of the present invention are advantageously utilized in order to collect a blood sample from a subject to allow anaerobic testing, such as arterial blood gas analysis. In order to perform a blood gas analysis, such as that utilized to test the cardiac functioning of the subject, the sharp end portion of the hypodermic needle is positioned to puncture the dermal layer of the subject, and to be positioned proximate to an arterial blood supply. Blood is caused to be aspirated through hypodermic needle 16 and into collection chamber 14 through operation of plunger 24 of FIG. 1, or through hypodermic needle 116 of FIG. 2 due to capillary action. Blood aspirated through hypodermic needles 16 or 116 is caused to be collected in chamber 12 or 112, respectively. The respective collection chambers 14 and 114 preferably further contain an anticoagulant material (not illustrated). Any air inadvertently aspirated into collection chambers 14 or 114 must be immediately expelled in order to maintain the anaerobic nature of the test. Once a suitable amount of blood is collected within the respective chambers, the syringe assembly 10 or 110 may be then transported to a laboratory for suitable testing of the blood sample.

As mentioned previously, because the blood is actually comprised of plasma and heavier solid blood cells, the solid portions of the blood tend to separate out of the blood mixture. The rate and the amount of sedimentation of the solid blood cells depends on many factors, including time, temperature, and the medical condition of the patient. In order to ensure the blood sample to be homogeneous prior to laboratory testing, the collection chamber 14 need only be inverted so as to cause the mechanical mixer 22 to travel through the blood mixture to float upon the top surface of the blood. Translation of the mechanical mixer 22 through the blood functions to mix the blood to thereby suspend the solid blood cells in the mixture. As the blood sample is readied for laboratory analysis, the syringe assembly, and in particular collection chamber 14 thereof, may be again inverted in order to cause translation of mixer 22 through the blood sample in order to ensure the blood is in a homogeneous state. Proper selection of the density of the mechanical mixer 22, and the size of the mixer 22 provides an effective stirring mechanism to insure that the blood sample is maintained in a homogeneous state. Because center aperture 32 permits the relatively gentle flow and agitation of blood as the mixer 22 is translated through the blood sample, trauma to the blood sample is minimized while maintaining the blood in a homogeneous state whereas in the mixing machines commonly used in the prior art, the blood samples, in particular, blood cells were often destroyed by overaggressive shaking and agitation.

Figure 8:
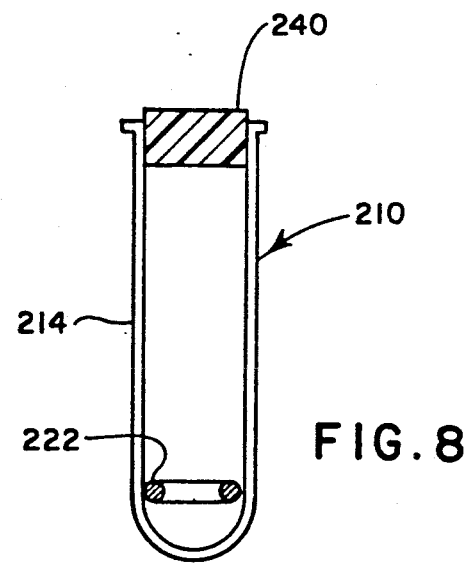
FIG. 8 is a perspective illustration, similar to those of FIGS. 1 and 2, but illustrating a third embodiment of the present invention wherein the mechanical mixer is used within a test-tube or similar container.

FIG. 8 illustrates a third embodiment of the fluid mixing assembly constructed in accordance with the present invention. In this embodiment, the assembly 210 includes a collection/mixing chamber 214 in the form of a test tube, graduated cylinder, or the like. The assembly 210 finds particular beneficial usage in industrial testing laboratories for such products as cosmetics, paints, and medicines. Upon filling of the chamber 214 to the desired level in order to obtain a sample for testing, the chamber is capped by a stopper means 240. During filling and capping, the mixer 222, which is of less density than the fluid being sampled, rises to float on the surface of the fluid. In order to mix the fluid, the chamber 214 is inverted and the mixer 222 is translated to the upper surface of the fluid as in the syringe assemblies of FIGS. 1 and 2.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. An assembly for collecting fluid sample and maintaining a fluid sample in homogeneity, said assembly comprising:
    means forming a barrel having an internal collection chamber for collection of the fluid sample therein;
    means for aspirating the fluid sample into said internal collection chamber; and
    mixing means including a fluid passageway positioned within said internal chamber to translate through the fluid sample by a relatively gentle flow and agitation of fluid flow through said passageway and thereby minimizing trauma to the fluid sample collected in the internal chamber, said mixing means having a preestablished constant density which is always less than the density of the fluid sample such that inversion of the means forming the barrel, once the fluid sample is collected in the internal collecting chamber, causes the mixing means to rise through the fluid sample to thereby mix the fluid sample and maintain the fluid sample in homogeneity.

2. A syringe assembly for collecting from a subject a blood sample comprised of plasma and blood cells and for maintaining the blood sample in a state of homogeneity, said syringe assembly including:
    means forming a barrel having an internal collection chamber for collection of the blood sample therein;
    a hypodermic needle for aspirating blood from the subject, said hypodermic needle having an end portion in fluid communication with said internal collection chamber for permitting collection of said blood aspirated by the hypodermic needle to be collected in said internal collection chamber; and
    a mechanical mixer including a fluid passageway positioned within the internal collection chamber to permit a relatively gentle flow and agitation of blood as the mixer translates aspirated blood in said collection chamber for maintaining the plasma and the blood cells comprising the blood sample in said state of homogeneity such that any portion of the blood sample may be utilized as a homogeneous and accurately representative specimen of the blood sample, said mechanical mixer having a constant density which is always less than the density of the blood sample such that inversion of the means forming the barrel once the blood sample together with the fluid flow passageway is collected in the internal collection chamber causes the disk member to rise through the blood sample with mixing by the relatively gentle flow and agitation of blood while minimizing trauma to the homogeneous blood sample.

3. A method for collecting a fluid sample from a fluid source, and for maintaining said fluid sample, once collected, in homogeneity, said method including the steps of:

selecting a mechanical mixer having a fluid passageway and a constant specific gravity which is always less than the specific gravity of the fluid sample to be collected;

arranging the mechanical mixer in a collection chamber for the fluid sample;

inverting an end portion of a hypodermic needle into a subject to position said end portion proximate to the fluid source from which said fluid sample is to be collected;

aspirating a desired amount of fluid from the fluid source through said hypodermic needle;

collecting said fluid aspirated through said hypodermic needle in a collection chamber, said collection chamber containing means for mixing the fluid sample collected;

inverting said fluid sample, once collected in said collection chamber in order to cause said mixing means to rise with a translating movement through the fluid sample and thereby mix with gentle flow and agitation the fluid sample to maintain homogeneity while minimizing trauma.

* * * * *